United States Patent [19]

Hartmann et al.

[11] Patent Number: 4,865,052
[45] Date of Patent: Sep. 12, 1989

[54] METHOD OF AND APPARATUS FOR MAKING A STREAM FROM PARTICLES OF THE TOBACCO PROCESSING INDUSTRY

[75] Inventors: Werner Hartmann, Neu Wulmstorf; Henning Möller, Hamburg, both of Fed. Rep. of Germany

[73] Assignee: Körber AG, Hamburg, Fed. Rep. of Germany

[21] Appl. No.: 930,251

[22] Filed: Nov. 12, 1986

[30] Foreign Application Priority Data

Nov. 13, 1985 [DE] Fed. Rep. of Germany ....... 3540144

[51] Int. Cl.⁴ .......................... A24C 5/18; A24C 5/31
[52] U.S. Cl. .................................. 131/844; 131/280; 131/905; 131/906; 131/908
[58] Field of Search .................... 131/84.4, 280, 905, 131/906, 908

[56] References Cited

U.S. PATENT DOCUMENTS 3,056,026 9/1962 Bigelow .............................. 131/905

Primary Examiner—V. Millin
Attorney, Agent, or Firm—Peter K. Kontler

[57] ABSTRACT

The density of a stream of tobacco particles at the underside of a foraminous belt conveyor is monitored by an array of X-ray detectors to generate signals each denoting the density of a different thin layer in successive increments of the stream. Such signals are processed into signals denoting the density of the entire stream, the filling power of tobacco, and the quantity of the surplus in the stream. The processed signals are used to adjust the trimmer which removes the surplus, to adjust the distributor which feeds the particles to the stream, to regulate the hardness of cigarettes and to adjust the quantity of the surplus.

52 Claims, 4 Drawing Sheets

METHOD OF AND APPARATUS FOR MAKING A STREAM FROM PARTICLES OF THE TOBACCO PROCESSING INDUSTRY

BACKGROUND OF THE INVENTION

The present invention relates to a method of and to an apparatus for making a stream from particles of the tobacco processing industry, particularly from particles of natural, reconstituted or substitute tobacco and mixtures thereof, or from particles which are used in the fillers of filter rods to produce mouthpieces for cigarettes, cigars, cigarillos and like rod-shaped smokers' products.

For the sake of simplicity, the following description will deal with the making of cigarettes. However, it is to be understood that the stream which is formed and processed in accordance with the present invention can be made from particles or fragments other than those constituting the smokable part of a plain or filter cigarette, cigarillo, cigar or cheroot.

It is well known to make a cigarette rod by showering or otherwise delivering fragments of tobacco leaves, fragments of reconstituted tobacco sheets and/or fragments of substitute tobacco onto a circulating air-permeable endless belt conveyor which travels along a suction chamber to attract a growing tobacco stream and to advance the stream past a trimmer which removes the surplus before the resulting trimmed or equalized stream is draped into a web of cigarette paper or the like and is subdivided into cigarettes of unit length or multiple unit length. It is also known to monitor the density of the trimmed stream, of the filler in the cigarette rod and/or of the fillers in discrete cigarettes, and to adjust the trimming device so as to ensure that the density of the tobacco filler will match or closely approximate a desired value. The density measurement is or can be carried out in such a way that the monitoring device ascertains the densities of successive increments or unit lengths of the stream, i.e., the densities of successive slabs of the stream extending at right angles to the direction of advancement of the stream along its path. Another known monitoring device comprises an array of detectors which are disposed in a row extending at right angles to the direction of travel of the stream and serve to generate signals denoting the densities of adjacent layers of the stream. The detectors generate signals in accordance with the intensity of radiation (particularly beta rays) which is capable of penetrating through the stream. The intensity of radiation which has penetrated through the stream is proportional to the density of the corresponding layers of the stream. The trimmer is movable relative to the path of the tobacco stream, i.e., nearer to or further away from the surface of the conveyor which attracts and transports the stream past the trimming station.

A method and apparatus of the above outlined character are disclosed in the commonly owned copending patent application Ser. No. 572,563 filed Jan. 18, 1984 now U.S. Pat. No. 4,785,830. In the apparatus of this copending application, fibrous material which is to form the stream is loosened in a distributor (also called hopper) and is showered into or otherwise delivered to a stream building station to be attracted by a driven air-permeable endless belt conveyor whereon the particles form a growing stream. The fully grown stream is advanced to the trimmer which removes the surplus, and the resulting trimmed stream is densified, draped to form a cigarette rod and conveyed through a cutoff to yield a succession of cigarettes of unit length or multiple unit length. The rod is monitored to ascertain the density of its filler, and the signals are used to adjust (when necessary) the position of the trimmer with reference to the conveyor.

The apparatus which is disclosed in the patent application Ser. No. 572,563, now U.S. Pat. No. 4,785,838, includes position-sensitive detectors which are designed to determine the density of several layers of the stream. Signals which are generated by the detectors furnish information concerning the distribution of density across the stream. Such signals are used to influence the formation of the stream in order to ensure the formation of a stream having a desired or optimum density profile.

As mentioned above, the density of the filler in the cigarette rod is normally determined with a beta ray detector. However U.S. Pat. No. 3,056,026 to Bigelow discloses a modified detector which operates with a source of X-rays and with an ionization chamber serving to receive radiation which has penetrated across the tobacco stream. Each of these conventional monitoring devices is capable of generating signals which denote the density profile of the monitored stream.

A drawback of conventional apparatus is that they do not embody any means which could be used to ascertain the filling power of tobacco and/or to influence the hardness of the cigarette rod and/or the hardness of individual smokers' articles. Moreover, heretofore known apparatus do not embody any suitable practical means for optimizing the quantity of surplus tobacco in the stream which advances toward the trimming station.

OBJECTS AND SUMMARY OF THE INVENTION

An object of the invention is to provide a novel and improved method of making and processing a stream of fibrous material in such a way that the parameters which determine the quality of the stream and of the products made from the stream can be influenced with a high degree of predictability and accuracy.

Another object of the invention is to provide a method which renders it possible to influence a variety of parameters of the stream and of the ultimate products in a simple, inexpensive and reliable way.

A further object of the invention is to provide a novel and improved method of making and manipulating a stream of natural, reconstituted and/or artificial tobacco particles in a cigarette rod making machine.

An additional object of the invention is to provide a method which renders it possible to produce rod-shaped articles of the tobacco processing industry in such a way that several different parameters of the articles match or closely approximate an optimum value.

Another object of the invention is to provide a novel and improved method of monitoring the density of a running stream of fibrous material, such as particles of tobacco or filter material for tobacco smoke.

An additional object of the invention is to provide a novel and improved method of ascertaining the filling power of particles of tobacco or other particulate material which is used and treated in the tobacco processing industry.

A further object of the invention is to provide a novel and improved method of influencing the hardness of cigarettes, filter rod sections and other rod-shaped articles of the tobacco processing industry.

Still another object of the invention is to provide a novel and improved method of regulating the quantity of the surplus of fibrous material in a stream which is about to be converted into the filler of a cigarette rod, filter rod or the like.

Another object of the invention is to provide a novel and improved apparatus for the practice of the above outlined method and to construct and assemble the apparatus in such a way that it can be installed in or used in conjunction with existing types of rod making machines of the tobacco processing industry.

A further object of the invention is to provide the apparatus with novel and improved means for ascertaining the density profile of a running stream of fibrous material, such as particles of natural, reconstituted and/or substitute tobacco or filter material for tobacco smoke.

Another object of the invention is to provide a rod making machine which embodies the above outlined apparatus.

An additional object of the invention is to provide a novel and improved density monitoring device for use in the above outlined apparatus.

Another object of the invention is to provide the apparatus with novel and improved means for processing signals which denote the density profile of a stream of fibrous material.

A further object of the invention is to provide the apparatus with novel and improved means for making the stream.

An additional object of the invention is to provide a novel and improved control system for evaluating signals which are generated by the aforementioned density monitoring device.

Another object of the invention is to provide the apparatus with novel and improved means for regulating the quantity of surplus in the stream.

A further object of the invention is to provide a novel and improved production line for the making of rod-shaped smokers' products which embodies the above outlined machine and apparatus.

An additional object of the invention is to provide the apparatus with novel and improved means for ascertaining the filling power of fibrous material which forms the stream, and with novel and improved means for utilizing signals which are indicative of the filling power.

One feature of the invention resides in the provision of a method of making and processing a stream of fibrous material (such as particles of tobacco) having a predetermined filling power. The method comprises the steps of advancing the stream longitudinally in a predetermined direction along a predetermined path (e.g., along a substantially horizontal path at the underside of the lower reach or flight of an endless foraminous belt conveyor whose lower reach is disposed below a suction chamber which attracts the fibrous material), monitoring the densities of different layers of the advancing stream in a succession of planes disposed at progressively increasing distances from a reference plane which bears a predetermined relationship to the path (the reference plane can coincide with the plane of the underside of the lower reach or flight of the endless belt conveyor) and generating first signals denoting the densities of the respective layers, generating a second signal constituting the sum of those first signals which denote the densities of successive layers of the aforementioned succession, starting with the layer nearest to the reference plane and terminating with a layer disposed at a predetermined distance from the reference plane, and converting the second signals into a third signal which denotes the filling power of the fibrous material (such conversion can take place in a filling power calculator in conjunction with a function generator).

The monitoring step can include measuring the densities of the layers at a plurality of locations forming a row extending substantially transversely of the predetermined direction.

As a rule, the stream contains a surplus of fibrous material, and the method then further comprises (or the method can further comprise) the steps of converting the third signal into a reference signal denoting a predetermined density of the stream, monitoring the density of the stream and generating an additional signal denoting the actual density of the stream, removing the surplus from the stream to convert the stream into an equalized stream, converting the equalized stream into a filler having a hardness which is a function of the quantity of fibrous material in the equalized stream, comparing the reference signal with the additional signal and generating a further signal which denotes the difference between the reference signal and the additional signal, and utilizing the further signal to change the quantity of removed surplus so as to maintain the hardness of the filler within a preselected range. Such method preferably further comprises the step of maintaining the intensity or another selected characteristic of the reference signal within a predetermined range; this includes reducing the intensity of the reference signal prior to the comparing step when the intensity exceeds the upper limit of the predetermined range and increasing the intensity of the reference signal prior to the comparing step when the intensity of the reference signal is below the lower limit of the predetermined range. The step of generating the additional signal preferably comprises generating a series of sum signals each constituting the sums of those first signals which denote the densities of successive layers of the succession of layers, starting with the layer nearest to the path, comparing successive sum signals with the reference signal, and replacing the reference signal with that one sum signal which at least matches the reference signal or with another suitable reference signal.

As mentioned above, the advancing step can include moving the stream by a conveyor having a stream-contacting surface in the reference plane.

The method can further comprise the steps of removing the surplus from the stream in a second plane which is spaced apart from the reference plane so as to form the aforementioned equalized stream, monitoring the density of the stream portion which is located outside of the area between the reference plane and the second plane (i.e., monitoring the density of the surplus), and generating a signal which denotes the quantity of the surplus. Such method can further include the steps of directing (e.g., showering) fibrous material into the path at a variable rate to thus form the stream, and varying the rate of delivery of fibrous material as a function of changes in the characteristics of the signal denoting the quantity of the surplus so as to maintain the quantity of the surplus in the stream within a given range. Still further, such method can comprise the steps of converting the equalized stream into a filler, monitoring at least one quality of the filler which is dependent upon the quantity of the surplus, and selecting the given range in such a way that its lower limit is sufficient to maintain the quality of the filler (or of the articles made from the filler) above a preselected minimum standard of acceptability. For example, the quality monitoring step can include generating signals which denote the monitored quality and the method then further comprises the steps of establishing a reference signal which denotes the minimum standard of acceptability, comparing the quality denoting signal with the reference signal denoting the minimum standard of acceptability, generating control signals which denote the difference between the compared signals, and utilizing the control signals to regulate the selecting step. Such method can further comprise the step of converting the filler into a succession of rod-shaped articles (e.g., plain cigarettes of unit length of multiple unit length), and the quality monitoring step can include monitoring the articles. By way of example, the article monitoring step can include ascertaining the densities of selected portions (particularly the head ends) of the articles.

The method can further comprise the steps of transporting a flow of fibrous material (e.g., a continuous relatively large mass of fragmentized tobacco leaves) along a second path which can be parallel to and can be disposed below the predetermined path, and transferring a portion of the flow from the second path into the predetermined path to form the stream. This renders it possible to monitor the density and/or filling power of a mass of fibrous material which is vibrated and/or otherwise agitated during advancement along the second path. The transferring step can include lifting the portion of the flow by a suction conveyor (e.g., an endless foraminous belt conveyor cooperating with a suction chamber), advancing the lifted portion of the flow in suspended condition along the predetermined path, and pneumatically condensing the lifted portion at least in the course of the density monitoring step. Such method can further comprise the step of returning (e.g, dropping) successive increments of the stream into the second path upon completion of the density monitoring and/or filling power determining step.

Another feature of the invention resides in the provision of a method of or process for making and processing a stream of fibrous material (such as particles of tobacco or filter material) which contains a surplus of fibrous material. The process comprises the steps of advancing the stream longitudinally (lengthwise) by the stream-contacting surface of a conveyor in a predetermined direction along a predetermined path, monitoring the densities of different layers of the advancing stream in a succession of planes disposed at progressively increasing distances from a reference plane which bears a predetermined relationship to the contacting surface (e.g., the reference plane can coincide with the stream-contacting surface) and generating first signals denoting the densities of the respective layers, removing the surplus from the stream in a plane (hereinafter called plane of removal) which is spaced apart from the reference plane to form an equalized stream, establishing a reference signal which denotes a predetermined density, generating a series of third signals constituting the sums of those first signals which denote the densities of successive layers of the succession (starting with the layer nearest to the reference plane), comparing successive third signals with the reference signal, and utilizing that one third signal which at least matches the reference signal to shift the plane of removal to a plane which is correlated to the plane of that layer whose monitoring has produced the first signal the addition of which to the preceding first signals has resulted in the generation of the one third signal (provided, of course, that the plane of removal requires a shifting toward or away from the reference plane).

The just described process can be used with advantage for the making and processing of a stream of fibrous material having a predetermined filling power. The step of establishing the reference signal can include converting a third signal which is the sum of a preselected number of first signals into a fourth signal denoting the filling power of fibrous material, converting the fourth signal into the reference signal, and replacing the reference signal with a different reference signal upon generation of the one third signal.

The process can further comprise the step of generating an additional signal denoting the quantity of the surplus and constituting the sum of those first signals which represent the densities of layers outside of the area between the reference plane and the plane of removal (i.e., the densities of those layers which together form the surplus). Such process can further comprise the steps of directing (e.g., showering or propelling) fibrous material into the path at a variable rate to thereby form the stream, and varying the rate of delivery of fibrous material into the path as a function of changes of the characteristics of the additional signal so as to maintain the quantity of the surplus within a given range (for example and preferably at a constant or nearly constant value). Such process can further comprise the steps of converting the equalized stream into a rod-like filler, monitoring at least one quality of the filler which is dependent upon the quantity of the surplus, and selecting the aforementioned given range so that its lower limit is sufficient to maintain the quality of the filler above a predetermined minimum standard of acceptability. The quality monitoring step can comprise generating further signals denoting the monitored quality, and the process can further comprise the steps of establishing a reference signal which denotes the minimum standard of acceptability, comparing the further signals with the reference signal denoting the minimum standard of acceptability, generating control signals denoting the differences between the further signals and the reference signal denoting the minimum standard of acceptability, and using the control signals to regulate the selecting step. Such process can include the step of converting the filler into a succession of rod-shaped articles (e.g., plain cigarettes, cigars, cigarillos, cheroots or filter rod sections of desired length), and the quality monitoring step includes or can include monitoring the articles. The article monitoring step can include ascertaining the densities of selected portions (e.g., ends) of the articles.

The process can further comprise the steps of transporting a flow of fibrous material along a second path and transferring a portion of the flow from the second path into the predetermined path to form the stream. The transferring step can include lifting the aforementioned portion of the flow by the conveyor, advancing the lifted portion of the flow in suspended condition along the predetermined path, and pneumatically condensing the lifted portion (at least in the course of the density monitoring step). Such process can further comprise the step of returning the stream (i.e., the lifted portion of the flow) into the second path upon completion of the density monitoring step and/or upon completion of the step of generating a signal which denotes the filling power of fibrous material.

A further feature of the invention resides in the provision of an apparatus for making and processing a stream of fibrous material (such as fragments of tobacco leaves or fibrous filter material for tobacco smoke) having a predetermined filling power. The apparatus comprises a conveyor which defines a predetermined path, means (such as a distributor or hopper) for delivering fibrous material into a first portion of the path so that the particles accumulate and form the stream which advances along the path, means for monitoring the densities of different layers of the stream downstream of the first portion of the path in a succession of planes disposed at progressively increasing distances from the conveyor including at least one row of detectors extending transversely of the path and each arranged to generate a first signal denoting the density of the adjacent layer, and control means for evaluating the first signals. The control means includes totalizing means for forming a second signal denoting the sum of a predetermined number of first signals which are generated by the detectors starting with the detector nearest to the conveyor, and calculator means for converting the second signal into a third signal denoting the filling power of the fibrous material. Each of the detectors can comprise a position sensitive transducer, and the monitoring means further comprises a source of radiation which penetrates through the stream to an extent which is a function of the density of the layers, and the radiation which has penetrated through the layers is directed against the respective detectors.

The delivering means is preferably arranged to form a stream which contains a surplus of fibrous material, and the apparatus further comprises means for removing the surplus from the stream in a second portion of the path downstream of the first portion so that the stream is converted into an equalized stream, and means for converting the equalized stream into a filler (such converting means includes means for densifying the stream). The control means of such apparatus further comprises function generator means for converting the third signal into a fourth signal denoting a predetermined density of the filler and means for adjusting the removing means as a function of a characteristic of the fourth signal when the hardness of the filler deviates from a predetermined value. This apparatus preferably further comprises a threshold circuit or an equivalent device which is connected to the function generator means and includes means for maintaining the intensity of the fourth signal within a predetermined range. Such apparatus can further comprise a source of reference signals denoting a predetermined hardness of the filler and serving to transmit such signals to the function generator means so as to influence the operation of the function generator means.

The apparatus can further comprise means for generating additional signals denoting the moisture content of fibrous material in the stream and for transmitting the additional signals to the function generator means to influence the fourth signal. The function generator means can comprise an empirically ascertained moisture-density matrix which influences the fourth signal as a function of one or more characteristics of the additional signals.

The aforementioned radiation source can constitute or include a source of X-rays, and the detectors can include a unidimensional array of diodes or they may constitute a CCD-array.

The delivering means can include means for transporting a flow of fibrous material along a second path at a level below the predetermined path, and the conveyor can include means for transferring a portion of the flow from the second path into the predetermined path so that the transferred portion of the flow constitutes the stream. The conveyor can include an endless foraminous belt having a lower reach adjacent the predetermined path, and a suction chamber which is disposed above the lower reach and serves to attract the aforementioned portion of the flow against the lower reach and to attract the stream to the lower reach during advancement of the stream past the monitoring means.

The means for removing the surplus is preferably adjustable, and such removing means is or can be disposed in a second portion downstream of the first portion of the path. The purpose of the surplus removing means is to convert the stream into the aforementioned equalized stream which is thereupon converted into a rod-like filler and the filler is converted into a series of rod-shaped articles. Conversion of the equalized stream into the filler preferably involves a densification and resulting increase of the hardness of the equalized stream. The control means of such apparatus can further comprise second totalizing means for generating a series of fourth signals constituting the sums of those first signals which denote the densities of successive layers of the aforementioned succession of layers (starting with the layer nearest to the conveyor), the aforementioned function generator means for converting the third signal into a fifth signal denoting a predetermined density of the stream, means for comparing successive fourth signals with the fifth signal and for generating sixth signals which denote the difference between the fourth signals and the fifth signal, and means for adjusting the removing means as a function of one or more characteristics of that sixth signal which at least matches the fifth signal. The control means of such apparatus can further comprise third totalizing means for generating a seventh signal denoting the sum of all first signals indicating the density of the surplus, means for establishing a reference signal which denotes the desired quantity of the surplus, and means for comparing the seventh signal with the reference signal representing the desired quantity of the surplus and for generating a further signal, and means for adjusting the delivering means (such as the aforementioned distributor or hopper) as a function of one or more characteristics of the further signal so as to maintain the quantity of the surplus within a predetermined range.

The apparatus can further comprise means for monitoring a quality of the filler which is dependent upon the quantity of the surplus and for influencing the further signal. The quality monitoring means can include means for monitoring a quality of the rodshaped articles, and the influencing means then includes or can include means for maintaining the quantity of the surplus at a value which ensures that the quality of the articles remains above a minimum standard of acceptability. For example, the monitoring of articles can involve detection of the density of their ends, and the surplus is then regulated with a view to ensure that the density of the ends at least matches a minimum acceptable density.

An additional feature of the invention resides in the provision of an apparatus for making and processing a stream of fibrous material (such as particles of natural, reconstituted and/or substitute tobacco). The apparatus comprises a conveyor which defines a predetermined path, means for delivering fibrous material into a first portion of the path so that the particles accumulate and form a stream which contains a surplus of fibrous material and advances along the path, adjustable trimming or equalizing means for removing the surplus in a first plane which is spaced apart from the conveyor in a second portion of the path downstream of the first portion so that the stream is converted into an equalized stream, means for monitoring the densities of different layers of the stream between the first and second portions of the path in a succession of planes disposed at progressively increasing distances from the conveyor and including detectors which form at least one row extending transversely of the path and each of which is arranged to generate a first signal denoting the density of the adjacent layer, and control means for evaluating the first signals. The control means comprises totalizing means for generating a series of second signals constituting the sums of those first signals which denote the densities of successive layers of the aforementioned succession starting with the layer nearest to the conveyor, a source of reference signals denoting a predetermined density of the stream, means for comparing successive second signals with the reference signals and for generating fourth signals denoting the difference between the second signals and the reference signals, and means for adjusting the surplus removing means in response to generation of that fourth signal whose intensity and/or another characteristic at least matches the reference signals. Each layer is disposed in a different plane, and the adjusting means can include means for moving the surplus removing means to that one of the different planes which contains the layer whose monitoring, totalizing and comparision has resulted in the generation of the fourth signal which at least matches the reference signals.

The control means can further comprise second totalizing means for generating a fifth signal denoting the sum of all first signals indicating the density of the surplus of fibrous material, means for establishing a second reference signal denoting the desired quantity of the surplus, means for comparing the second reference signal with the fifth signal and for generating a seventh signal, and means for adjusting the delivering means (such as a distributor or hopper in a filter rod making machine) as a function of the intensity or another characteristic of the seventh signal in order to maintain the quantity of the surplus within a predetermined range. Such apparatus further comprises means for converting the equalized stream into a rod-like filler, and means for directly or indirectly monitoring a quality of the filler which is dependent upon the quantity of the surplus and for influencing the seventh signal. If the apparatus further comprises means for converting the filler into a plurality of rod-shaped articles, the quality monitoring means can include means for monitoring a quality of the articles, and the influencing means then comprises means for maintaining the surplus at a value such that the quality of the articles remains above a minimum standard of acceptability. For example, the quality monitoring means can monitor the density of the ends of plain cigarettes of unit length or multiple unit length.

The means for monitoring the densities of different layers of the stream can further comprise a source of X-rays which is arranged to direct radiation against the stream so that the radiation penetrates through the stream and impinges upon the detectors with an intensity which is a function of the density of the respective layers. The detectors can include a unidimensional array of diodes or they may constitute a CCD-array.

The delivering means can include means for transporting a flow of fibrous material along a second path, particularly at a level below the predetermined path, and the conveyor can comprise means for transferring a portion of the flow from the second path into the predetermined path so that the transferred portion of the flow constitutes the stream. Such conveyor can include an endless foraminous belt having a lower reach or flight adjacent the predetermined path, and a suction chamber which is disposed above the lower reach and serves to attract the aforementioned portion of the flow against the lower reach and to attract the stream to the lower reach during advancement of the stream past the means for monitoring the densities of the layers of the stream.

The novel features which are considered as characteristic of the invention are set forth in particular in the appended claims. The improved apparatus itself, however, both as to its construction and its mode of operation, together with additional features and advantages thereof, will be best understood upon perusal of the following detailed description of certain specific embodiments with reference to the accompanying drawing.

DESCRIPTION OF THE PREFERRED EMBODIMENT

Figure 1:
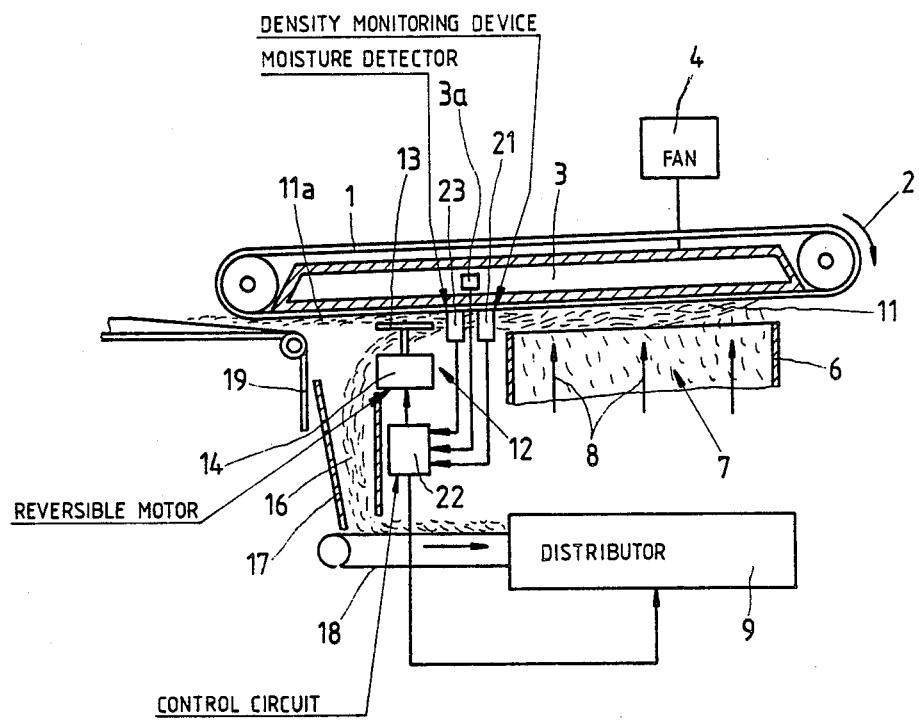
FIG. 1 is a schematic partly elevational and partly longitudinal vertical sectional view of an apparatus which embodies the invention and is used in a cigarette making machine.

FIG. 1 shows schematically an apparatus which embodies one form of the present invention. The structure which is shown in FIG. 1 includes a stream building or growing arrangement which is of the type used in many presently known cigarette rod making machines, e.g., in a machine known as PROTOS which is manufactured by the assignee of the present application. A more detailed description of such machine and of the stream building arrangement can be found, for example, in the aforementioned copending patent application Ser. No. 572,563 now U.S. Pat. No. 4,785,830.

The means for advancing a continuous stream 11 of fibrous material in the direction of an arrow 2 comprises an endless foraminous belt conveyor 1 having an elongated lower reach disposed above the discharge end of a substantially vertical duct 6 constituting a means for delivering loosened fragments of tobacco from a distributor 9 (also called hopper). The lower reach of the conveyor 1 travels below the foraminous bottom wall of a suction chamber 3 which is connected with the intake of a fan 4 or another suitable suction generating device 4. Streamlets of air which flow through the lower reach of the conveyor 1 and into the suction chamber 3 attract the fragments or particles of tobacco leaves, reconstituted tobacco and/or substitute tobacco so that such particles form a growing stream which is fully grown at the left-hand end of the outlet at the upper end of the duct 6. The directions in which the particles of tobacco are propelled and/or drawn in the duct 6 toward the underside of the lower reach of the conveyor 1 and/or onto the growing stream of tobacco particles on such lower reach are indicated by arrows 8. The particles form a shower 7 of uniformly or nearly uniformly distributed fibrous material which is fed at a variable rate in a manner and for the purposes set forth in the following passages of the description. The length of the stream building zone below the lower reach of the conveyor 1 is determined by the length of the outlet of the duct 6, as seen in the direction of the arrow 2. The fully grown stream 11 advances into the range of a surplus removing device 12 (hereinafter called trimmer or equalizer for short) which has one or more rotary tobacco removing discs 13 and a reversible motor 14 or analogous adjusting means for changing the position of the trimmer with reference to the lower reach of the conveyor 1 and for thus changing the quantity of surplus tobacco 16 which is removed by the discs 13. The trimmed or equalized stream is denoted by the character 11a.

The details of the distributor 9 form no part of the present invention. This distributor can be constructed and can operate in a manner as disclosed in the copending patent application Ser. No. 572,563, as known from the aforementioned PROTOS machine, and as disclosed in numerous granted United States letters Patent of the assignee. The distributor 9 receives surplus tobacco 16 by way of a funnel or chute 17 and a belt conveyor 18 which is mounted below the discharge end of the funnel 17.

The equalized tobacco stream 11a is transferred onto a running web 19 of cigarette paper or other suitable wrapping material and is caused to advance through a wrapping mechanism (not shown) wherein the web is converted into a tube which surrounds the resulting rod-like filler and forms therewith a continuous cigarette rod which is caused to pass through a conventional cutoff to be subdivided into cigarettes of unit length or multiple unit length. The construction of the wrapping mechanism and of the cutoff forms no part of the invention. Such units can be of the type as used in the PROTOS machine. The wrapping mechanism and the cutoff are shown schematically in the copending application Ser. No. 572,563, together with a density monitoring device for the cigarette rod.

In accordance with a feature of the invention, the apparatus of FIG. 1 further comprises a measuring or monitoring device 21 which is disposed between the stream building zone (duct 6) and the trimmer 12 to ascertain the density profiles of successive unit lengths of the fully grown tobacco stream 11. The output of the density monitoring device 21 is connected with one input of a control unit or evaluating means 22 having at least one first output for transmission of signals which are used to actuate the adjusting motor 14 of the trimmer 12 and at least one second output for transmission of signals which are used to regulate the operation of the distributor 9.

The density monitoring device 21 is located upstream of a moisture detector 23 whose output is connected with a second input of the control unit 22 and which serves to transmit signals denoting the actual moisture content of unit lengths of the stream 11 ahead of the trimming or equalizing station. Such signals are used to correct or modify signals which are transmitted by one or more outputs of the control unit 22. Moisture detectors of the type capable of being used in the apparatus of FIG. 1 are manufactured by the assignee of the present application.

Figure 3:
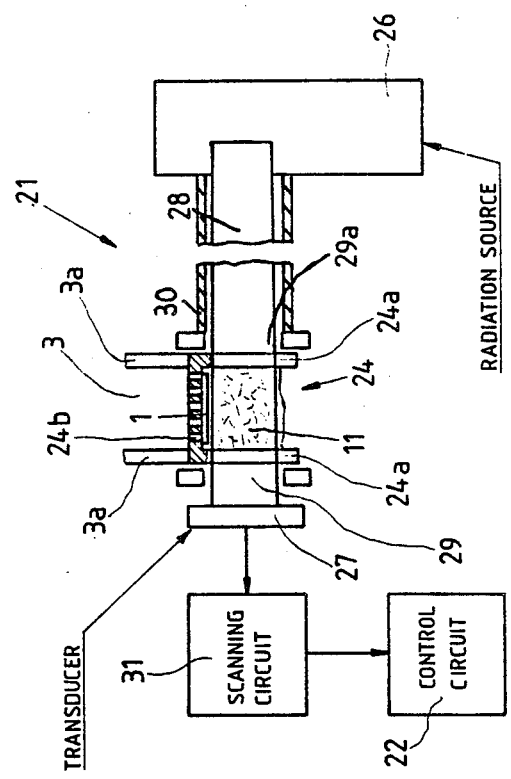
FIG. 3 is a schematic transverse vertical sectional view of the density monitoring device in the apparatus of FIG. 1.

FIG. 3 shows the details of a presently preferred embodiment of the density monitoring device 21 which can be used in the apparatus of FIG. 1. The lower reach of the conveyor 1 travels at the underside of the air-permeable bottom wall 24b of an inverted U-shaped channel 24 having sidewalls 24a which flank the tobacco stream 11 at the underside of the lower reach of the conveyor 1. The bottom wall 24b is adjacent to or forms an integral or detachable part of the bottom wall of the suction chamber 3 whose sidewalls are shown at 3a. A radiation source 26 is disposed at one side of the channel 24 to transmit a beam 28 of radiation which penetrates through the stream 11 and reaches a transducer 27 which transmits electric signals denoting the intensity of radiation which has penetrated through the stream 11. The transducer 27 is located at the opposite side of the channel 24 in the path of radiation which has penetrated through the stream 11, and the beam 28 is flanked by collimating diaphragms 29 and 29a and is focused by a shield 30. In the embodiment of FIG. 3, the radiation source 26 is or includes a conventional X-ray tube. Those portions of the sidewalls 24a which are located in the path of propagation of the beam 28 of X-rays constitute windows which are permeable to such radiation; to this end, portions of the sidewalls 24a can consist of or can contain panels or sheets made of or containing titanium.

Figure 2:
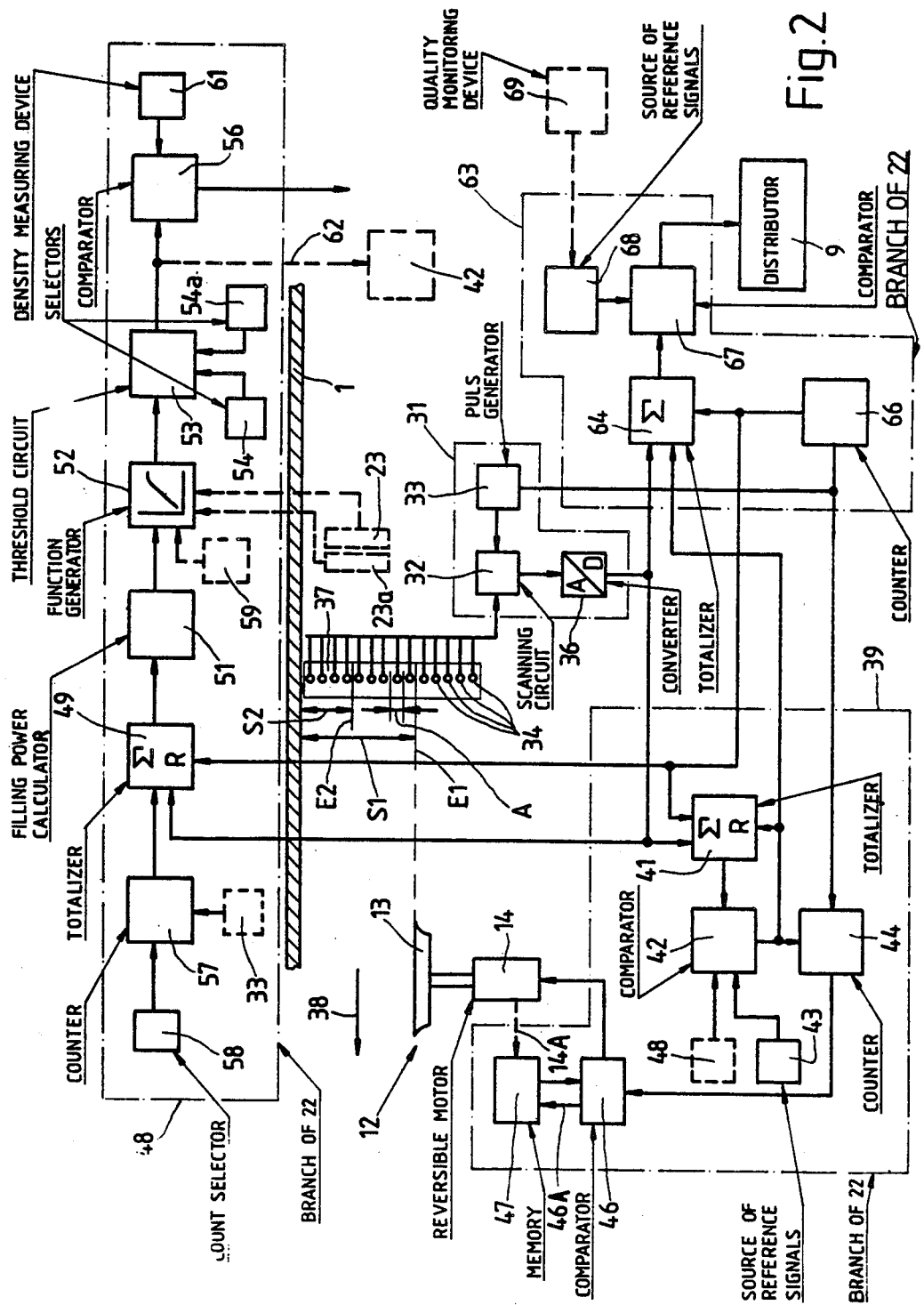
FIG. 2 is a block diagram of the control unit in the apparatus of FIG. 1.

As shown in FIG. 2, the density monitoring device 27 can comprise an unidimensional diode- or CCD-array 37 whose position-sensitive constituents or detectors 34 form a row extending at right angles to the plane of the lower reach of the conveyor 1 and disposed at different distances from such plane. The detectors 34 of the array 37 monitor the adjacent layers A of the advancing stream 11 and transmit signals denoting the densities of the respective layers.

FIG. 3 shows that signals which are generated by the transducer 27 (detectors 34) of the density monitoring device 21 are transmitted to the input of a scanning circuit 31 whose output is connected with the corresponding input of the control unit 22. Referring again to FIG. 2, the scanning circuit 31 comprises an addressing circuit 32 which addresses the individual detectors 34 of the array 37 in the density monitoring device 21 at a frequency determined by the pulses of a timing pulse generator 33. The signals which are generated by the detectors 34 of the array 37 are analog signals which are converted in an analog-digital converter 36 serving to transmit digital signals to several branches of the control unit 22.

As mentioned above, each detector 34 generates signals denoting the density of the adjacent layer A of the advancing tobacco stream 11, i.e., at a different distance from the plane of the underside of the lower reach of the conveyor 11. The plane of the underside of the lower reach of the conveyor 1 can be said to constitute a main or primary reference plane; however, it is equally possible to select a different reference plane which is located at a predetermined distance from the underside of the lower reach of the conveyor 1. By way of example, the array 37 can comprise a total of 1024 detectors 34, e.g., diodes which are sensitive to X-rays. The detectors 34 monitor a total of 1024 different layers A of the running stream 11, and each such layer is disposed at a different distance from the main or primary reference plane. The direction in which the stream 11 advances past the detectors 34 is indicated in FIG. 2 by an arrow 38. The trimmer 12 is located downstream of the diodes 34, as seen in the direction of travel of the stream 11 from the stream building zone (above the duct 6) toward the wrapping mechanism wherein the cigarette paper web 19 is draped around the equalized stream 11a to form a continuous rod which is subdivided into rod-shaped articles of desired length.

The source 26 of radiation, the beam 28 and the detectors 34 (transducer 27) are shown in FIG. 3 in a very schematic way. As a rule, position sensitive monitoring of density in successive layers A of the tobacco stream 11 (as a function of monitored height of the stream 11) can be carried out with a higher degree of accuracy if the rays issuing from the source 26 are parallel to each other during penetration through the stream 11 and during impingement upon the corresponding detectors 34. By way of example, this can be accomplished by placing the source 26 at a substantial distance from the stream 11 and transducer 27. It is often preferred or desirable to employ the aforementioned shield 30 (e.g., a tubular guide) which ensures that radiation issuing from the source 26 and reaching the stream 11 includes parallel rays. If the length of the guide 30 is increased, the rays which advance therethrough are more likely to be parallel to each other, i.e., the percentage of parallel rays which penetrate through the stream 11 is increased. This increases the reliability or accuracy of signals which are transmitted by the detectors 34 and are intended to be indicative of the density and mass of tobacco particles in the respective layers A.

All such details of the control unit 22 which are necessary for understanding of the invention are shown in FIG. 2. This unit comprises a first branch 39 including a summing or totalizing circuit 41, a first signal comparing stage or comparator 42, a source 43 of reference signals whose output is connected with the corresponding input of the stage 42, a resettable counter 44, a second signal comparing stage or comparator 46 and a memory 47 for storage of an actual value signal denoting the momentary position of the trimming plane, i.e., the distance of the plane of the discs 13 from the aforementioned primary reference plane.

When the improved apparatus is in use, the timing pulse generator 33 transmits pulses which determine the frequency at which the detectors 34 of the array 37 are addressed by the circuit 32, one after the other starting with the detector 34 which is nearest to the primary reference plane and proceeding in a direction at right angles to and away from such plane. Each of the detectors 34 transmits a signal denoting the density of the respective layer A of the stream 11 at the density monitoring station. Analog signals which are transmitted by successive detectors 34 are individually converted (by 36) into digital signals which are transmitted to the summing circuit 41 of the branch 39. The circuit 41 totals the densities which are denoted by signals from successive detectors 34 and transmits, after receipt of a digital signal, a corresponding signal (denoting the sum of theretofore received digital signals) to the corresponding input of the first signal comparing stage 42. Another input of the first stage 42 receives a reference signal from the source 43, and such reference signal is indicative of the desired or optimum density of the stream 11. If the intensity or another characteristic of the sum of signals which are transmitted by a given number of detectors 34 does not match the corresponding characteristic of the reference signal, the circuit 32 addresses additional (successive) detectors 34, and the circuit 41 continues to add the corresponding digital signals to the sum of previously received signals. At the same time, the counter 44 counts the number of pulses which are transmitted by the timing pulse generator 33 and thus contains information pertaining to the total number of addressed detectors 34 and the last detector 34 which has already transmitted a density signal to the analog-digital converter 36 and hence to the summing circuit 41 of the branch 39. In other words, the counter 44 contains information denoting (a) the total number of layers A whose densities were measured and corresponding signals transmitted to the summing circuit 41 and (b) the locus of that detector 34 which was last to transmit a signal to the circuit 32 and hence to the converter 36 and summing circuit 41.

When the intensity or another characteristic of the signal which is transmitted by the summing circuit 41 matches or exceeds the corresponding characteristic of the reference signal from the source 43, the stage 42 transmits a signal which arrests the summing circuit 41 and the counter 44. The output of the counter 44 then transmits a signal denoting that detector 34 and that layer A whose monitoring has resulted in the transmission of the last density signal to the summing circuit 41. The corresponding layer A is disposed in a plane E1 which is indicative of the height of that portion of the stream 11 that was needed to generate a combined density signal corresponding to the reference signal from 43 denoting the desired or optimum density of the stream. The height of the corresponding portion of the stream 11 is denoted in FIG. 1 by the character S1.

The signal which is then transmitted by the counter 44 denotes the corresponding layer A and the associated detector 34, i.e., such signal denotes the plane E1 which is located at the distance S1 from the primary reference plane corresponding to the plane of the underside of the lower reach of the conveyor 1. The signal at the output of the counter 44 is transmitted to the second signal comparing stage 46 wherein the signal is compared with the signal which is stored in the memory 47 and denotes the momentary position of the plane of the discs 13 forming part of the trimmer 12. If the signal from the signal comparing stage 46 deviates from the signal which is stored in the memory 47, the adjusting motor 14 is caused to shift the discs 13 to a level which matches or is otherwise properly related to the level of the plane E1. At the same time, the information in the memory 47 is erased and the memory 47 stores a fresh signal which denotes the new position of the plane of the discs 13.

A similar result can be achieved by providing the adjusting motor 14 or another part of the trimmer 12 with a level detector which transmits appropriate signals to the memory 47 (note the broken line 14A) so that the connection 46A between the second signal comparing stage 46 and the memory 47 can be omitted. The level detector which is embodied in, or is associated with, the adjusting motor 14 or with another part of the trimmer 12 can be of any conventional design and is not specifically shown in FIG. 2.

The just described system renders it possible to adjust the level of the discs 13 relative to the level of the underside of the lower reach of the conveyor 1 with a very high degree of accuracy, i.e., as a highly accurate function of the density of the stream 11. The just discussed density monitoring device 21 can be used in lieu of, or in conjunction with, a conventional density monitoring device (not shown) which includes means for ascertaining the density of successive increments of the finished cigarette rod and/or of discrete cigarettes which are obtained in response to severing of the cigarette rod. The conventional density monitoring device can comprise a source of beta rays at one side and an ionization chamber at the opposite side of the path of travel of the cigarette rod or at the opposite side of the path of travel of discrete cigarettes of unit length or multiple unit length. Signals which are generated by the conventional density monitoring device downstream of the trimming and wrapping stations can be used to correct the level of the discs 13 if such level (after adjustment in response to signals from the second signal comparing stage 46) deviates from an optimum level which is needed to ensure the making of a cigarette rod or cigarettes having an optimum density.

The improved control unit 22 further comprises a second branch 48 including a summing or totalizing circuit 49, a filling power calculator 51, a function generator 52, a threshold circuit 53 with upper and lower threshold limit selectors 54 and 54a, and a signal comparing stage or comparator 56. The summing circuit 49 has an input which is connected with the output of a counter 57 which is adjustable by a selector 58. The branch 48 serves to generate a filling power signal which can be used to regulate the hardness of the stream. To this end, the selector 58 can select a second plane E2 which is located at a distance S2 from the primary reference plane (here coinciding with the plane of the underside of the lower reach of the conveyor 1). The distance of the primary reference plane from the plane E2 corresponds to the sum of a predetermined number of layers A, i.e., to the sum of a predetermined number of detectors 34 of the array 37. Such predetermined number is selected by the selector 58 for the counter 57 which transmits a signal to the summing circuit 49 when the predetermined (maximum) number is reached. The counter 57 has a further input which is connected with the output of the timing pulse generator 33 (shown in FIG. 2 by solid lines adjacent the scanning circuit 32 and in broken lines adjacent the counter 57) so that the counter can count the number of detectors 34 which have transmitted density signals to the analog-digital converter 36 and to the summing circuits 41, 49 starting with the detector 34 nearest to the primary reference plane and proceeding with successive detectors 34 in a direction away from the underside of the lower reach of the conveyor 1.

The summing circuit 49 of the branch 48 totalizes the signals which are transmitted by successive detectors 34 of the array 37 up to and including the last detector within the distance S2 between the primary reference plane and the plane E2 i.e., up to and including the last detector 34 of the number which is selected in advance by the selector 58 for the counter 57. At such time, the counter 57 transmits a signal which arrests the summing circuit 49 whose output then transmits a signal (denoting the sum of signals transmitted by the detectors 34 within the distance S2) to the corresponding input of the filling power calculator 51. The calculator 51 relates the signal from the summing circuit 49 to the volume of the stream 11 (such volume is determined by the position of the reference plane E2 and the geometric configuration of the stream 11) and processes the information into a signal which is indicative of filling power of the stream. The signal which denotes the filling power of the stream is transmitted to the function generator 52 which is implemented by an empirically determined filling power-density-hardness matrix and which, based on such relationship, transmits a reference signal denoting the desired density of the stream in order to achieve a predetermined hardness. The reference signal denoting the desired density of the stream is transmitted to the signal comparing stage 56 wherein such signal is compared with a signal denoting the actual density of the stream, and the resulting signal is used to regulate the level of the plane of the discs 13 relative to the primary reference plane. The signal denoting the actual density of the stream can be obtained by monitoring the density of the cigarette rod and/or the density of discrete cigarettes, e.g., in a conventional manner by means of a beta ray detector including a source of beta rays and an ionization chamber.

The function generator 52 is further connected with a source 59 of reference signals denoting a preselected hardness of the filler.

If the tobacco which is supplied by way of the duct 6 has a high filling power, the desired hardness of the cigarette rod can be reached while the density of the filler of the rod is relatively low. This leads to the making of lightweight cigarettes. Inversely, when the filling power of tobacco which is supplied to the stream building zone is relatively low, the desired hardness of the filler of the cigarette rod can be reached only by increasing the density of the filler, i.e., by making cigarettes whose weight is rather high. In order to ensure that the weight of cigarettes will be kept within a prescribed range while allowing for a regulation of the hardness of the filler in the aforedescribed manner, the signal which is transmitted by the function generator 52 is caused to enter the corresponding input of the threshold circuit 53 which, in turn, transmits a signal that does not exceed the upper limit as determined by the selector 54 and does not drop below the lower limit as determined by the selector 54a. In other words, the intensity or another characteristic of the signal which is transmitted to the threshold circuit 53 and thereupon reaches the signal comparing stage 56 does not exceed a value which is determined in advance by the selector 54 and does not drop below the value which is chosen in advance by the selector 54a.

The filling power of tobacco and the hardness f the cigarette rod filler are functions of the moisture content of tobacco particles which are supplied to the stream building zone at the outlet of the duct 6. The reference signal which denotes the density of the stream 11 and is transmitted by the function generator 52 is corrected or modified in accordance with the signal which is generated by the moisture detector 23 so as to take into consideration the actual moisture content of tobacco forming the stream 11. The output of the moisture detector 23 transmits signals to the corresponding input of the function generator 52 wherein the signals are utilized to modify the signal at the output of the function generator in accordance with an empirically ascertained relationship between the moisture content of tobacco particles and the hardness of the stream and/or filling power of tobacco.

FIG. 2 shows that the stage 56 of the second branch 48 of the control unit 22 compares signals from the threshold circuit 53 with reference signals which are transmitted by a conventional density measuring device 61, e.g., the aforediscussed density measuring device 5 which is adjacent the path of travel of the cigarette rod and/or discrete cigarettes and employs a source of beta rays and an ionization chamber of known design. As shown in FIG. 2 by a broken line 62, the signal at the output of the function generator 52 (and more particularly the signal at the output of the threshold circuit 53) can also be transmitted to the signal comparing stage 42 of the branch 39 in lieu of signals which are transmitted by the source 43 of reference signals. In other words, the reference signal denoting the desired density of the stream 11 can be furnished by the function generator 52. FIG. 2 shows the signal comparing stage 42 twice (once by solid lines and once by broken lines) so as to avoid the need for illustration of numerous connections between the solid-line stage 42 and the output of the threshold circuit 53. For the same reason, the entire branch 48 of the control unit 22 is shown in FIG. 2 for a second time by broken lines adjacent the signal comparing stage 42 of the branch 39.

The utilization of function generator 52 as a source of reference signals in lieu of the source 43 exhibits the advantage that direct regulation of the level of the trimming discs 13 by way of the branch 39 of the control unit 22 is combined with the regulation of hardness by way of the branch 48. Thus, a regulation of the position of the trimmer discs 13 as a function of signals which are transmitted by the branch 39 entails the making of a stream or filler having a predetermined or optimum hardness.

The control unit 22 comprises an additional branch 63 including a summing or totalizing circuit 64 one input of which receives signals from the analog-digital converter 36, a counter 66 one input of which is connected with the output of the timing pulse generator 33, a comparator or signal comparing stage 67 one input of which receives signals from the output of the summing circuit 64, and a source 68 of reference signals connected to the other input of the stage 67. The output of the signal comparing stage 67 transmits signals which are used to regulate the operation of the distributor or hopper 9 so as to alter the quantity of tobacco particles which form the shower 7 and are admitted into the stream building zone.

The purpose of the branch 63 is to monitor and regulate the quantity of surplus 16 in the stream 11. As already explained above, tobacco particles which are located between the underside of the lower reach of the conveyor 1 and the plane E1 (i.e., the plane of the discs 13 of the trimmer 12) are converted into the filler of the cigarette rod and thereupon into the fillers of discrete cigarettes of unit length or multiple unit length. The density of the filler matches that which is denoted by the reference signal supplied by the source 43 or by the output of the branch 48 and utilized in the stage 42 for comparison with the signal denoting the sum of signals formed by the circuit 41 of the branch 39. The surplus 16 is constituted by those particles of tobacco which are located below the reference plane E1, as seen in FIG. 2, i.e., at a level below the plane of the discs 13. In order to ascertain the quantity of tobacco particles which form the surplus 16, the signal at the output of the summing circuit 41 in the branch 39 starts the summing circuit 64 whereby the latter totalizes the signals which are generated by detectors 34 located below the level of the plane E1 (as seen in FIG. 2). Thus, the summing circuit 64 totalizes the signals which are transmitted by the analog-digital converter 36 after the summing circuit 41 is deactivated because the intensity of another characteristic of the signal which appears at its output matches or exceeds the intensity or another characteristic of the reference signal from the source 43 or branch 48. The counter 66 counts the number of pulses which are transmitted by the timing pulse generator 33 after the summing circuit 64 is started following stoppage of the summing circuit 41.

When the circuit 64 receives a signal from the last detector 34, i.e., when the signal at the output of the circuit 64 denotes the density and quantity of tobacco forming the surplus 16, the counter 66 arrests the circuit 64 and causes the latter to transmit a signal to the signal comparing stage 67. The stage 67 compares the incoming signal (denoting the sum of signals transmitted by the detectors 34 below the plane E1) with the signal from the source 68 of reference signals. In the event of deviations of the signal transmitted by the circuit 64 from the signal which is supplied by the source 68, the output of the stage 67 transmits a signal to the distributor 9 in order to change (increase or reduce) the rate of delivery of particles which form the shower 7 in a manner well known from the art of cigarette rod making machines. Thus, the branch 63 of the control unit 22 ensures that the quantity of particles forming the surplus 16 remains at least substantially constant. Moreover, signals which are transmitted by the source 68 can be readily selected in such a way that the quantity of surplus 16 is reduced to a minimum which is still acceptable, i.e., which does not adversely influence the quality of the filler in the cigarette rod. A reduction of the surplus 16 to an acceptable minimum and retention of the quantity of surplus at such value is desirable and advantageous because it amounts to a more economical utilization of tobacco.

In order to ensure that a reduction of the quantity of surplus 16 will not result in a reduction of the quality of the tobacco stream and rod-shaped articles which are obtained from the tobacco stream, it is desirable to provide at least one measuring or monitoring device 69 (shown in FIG. 2 by broken lines) which is used to automatically adjust the intensity and/or other characteristics of the reference signal which is transmitted by the source 68. The device 69 is designed to monitor at least one characteristic of the filler in the cigarette rod (and/or of the fillers in the cigarettes) which is dependent upon (i.e., which can be influenced by) the quantity of the surplus 16. If the device 69 transmits a signal which denotes that the monitored characteristic of the filler is unsatisfactory, the source 68 is adjusted accordingly to transmit a different reference signal which normally entails an increase of the quantity of tobacco particles in the surplus 16. By way of example, the device 69 can be designed to monitor the ends of finished cigarettes for density, especially if the cigarette rod making machine embodying the apparatus of the present invention is designed to produce cigarettes with so-called dense ends. Devices which can monitor the densities of cigarette ends are well known and are described in numerous patents of the assignee.

The signal which is generated by the counter 66 to arrest the summing circuit 64 (such signal denotes the termination of the addressing cycle by the scanning circuit 32) is further transmitted to the summing circuits 41, 49 as well as to the corresponding inputs of the counters 44, 57, 66 so that all three summing circuits and all three counters are reset to zero to be ready for the start of the next scanning cycle. Each cycle can be completed within a few milliseconds.

An important advantage of the branch 39 of the control unit 22 is that it can monitor the density of the stream 11 and can process the signals from the detectors 34 prior to removal of the surplus, i.e., while the stream is still open. This renders it possible to locate the trimming discs 13 with a high degree of accuracy as a result of advance measurement of the density of the stream, i.e., the likelihood of producing even a short series of cigarettes wherein the density of fillers is unsatisfactory is very remote or nil. In other words, and since the measurement of density takes place ahead of the trimming station, a density measurement (such as by the device 61 in the branch 48 of the control unit 22) upon the cigarette rod and/or finished articles is merely a safety undertaking because a highly accurate determination of density of the equalized stream 11a can be carried out prior to removal of the surplus, i.e., ahead of the first processing station for the particles of the stream 11.

The branch 48 of the control unit 22 exhibits the advantage that it renders it possible to calculate the filling power of tobacco particles and to utilize the signals denoting the filling power in the aforedescribed manner. If desired, signals which denote the filling power of tobacco particles can be merely displayed on a screen, or the displaying can take place in addition to the aforediscussed processing of such signals.

A desirable feature of the utilization of converted signals from the function generator 52 as reference signals denoting a predetermined density of the stream 11 (note the broken-line position of the branch 48 in FIG. 2) is that this even further ensures the making of highly satisfactory cigarettes because the relationship between the filling power and density of the cigarettes is established at all times or at least at the very start of the operation. Signals which are transmitted by the source 43 of reference signals can be generated as a result of a measurement of the density of satisfactory cigarettes. Signals denoting the filling power are used (or can be used) to influence the output signal of the comparator 42 and hence the position of the trimming discs 13. Moreover, signals which denote the filling power are used to regulate the hardness of the cigarette rod and cigarettes. This not only enhances the quality of the cigarettes but also ensures a highly economical utilization of tobacco.

The threshold circuit 53 and its selectors 54, 54a ensure that the machine which embodies the apparatus of the present invention will not turn out cigarettes whose weight is less than acceptable just because the filling power of tobacco particles is very high, or that the machine will not turn out cigarettes whose weight is excessive just because the fillers of such articles contain tobacco particles whose filling power is low (i.e., the density of such cigarettes had to be increased in order to achieve the desired hardness).

The feature that the signal from the branch 48 to the comparator 42 is or can be replaced with a different reference signal when the signal at the output of the comparator 42 matches the signal at the output of the branch 48 ensures that the initial adjustment of the level of the trimming discs 13 is determined by the signals which denote the filling power; this results in the making of cigarettes having a predetermined hardness. The placing of the first reference plane into the plane of the underside of the lower reach or flight of the conveyor 1 simplifies the controls.

An advantage of the branch 63 of the control unit 22 is that it allows for simple, accurate and convenient determination of the quantity of tobacco particles in the surplus 16 and for the generation of corresponding signals which are then processed in the aforedescribed manner, i.e., to regulate the operation of the distributor 9 and hence the rate of delivery of tobacco particles to the stream building zone as well as to allow for a comparison of signals from the totalizer 64 with signals (from the source 68) which are influenced by signals denoting one or more characteristics of the cigarette rod and/or cigarettes, namely one or more characteristics which are directly or indirectly influenced by the quantity of tobacco particles in the surplus. As a rule, the manufacturers will tend to select the quantity of the surplus in such a way that the surplus is reduced to a minimum. However, such optimizing of the quantity of surplus 16 will be sacrificed if the signals from the monitoring device 69 indicate that the quality of the cigarette rod and of the cigarettes is below par. As mentioned above, a characteristic of cigarettes which is influenced by the quantity of the surplus is the hardness (density) of the ends of cigarettes if the machine which employs the improved apparatus is used to make cigarettes with dense ends.

Advance and direct determination of the optimum position of the trimming discs 13 constitutes a very important and desirable feature of the improved method and apparatus. Such optimum position is that position which guarantees the making of an equalized stream having a predetermined optimum density. At the very least, this enhances the accuracy of selection of a desirable density for the equalized stream 11a and for the articles which are made therefrom.

It has been found that the control unit 22 (and more specifically its branch 48) ensures the establishment of an optimal, or at least highly satisfactory, relationship between the density and hardness of the finished products. The regulation of hardness is enhanced due to the provision of the moisture detector 23 whose signals are processed in the function generator 52 so that the signals which are transmitted to the threshold circuit and thence to the comparator 42 are influenced by the actual moisture content of tobacco particles which form the stream 11.

Monitoring of the density of the stream 11 ahead of the trimming station allows for a highly accurate regulation of the density of fillers in the cigarette rod and discrete cigarettes.

Figure 4:
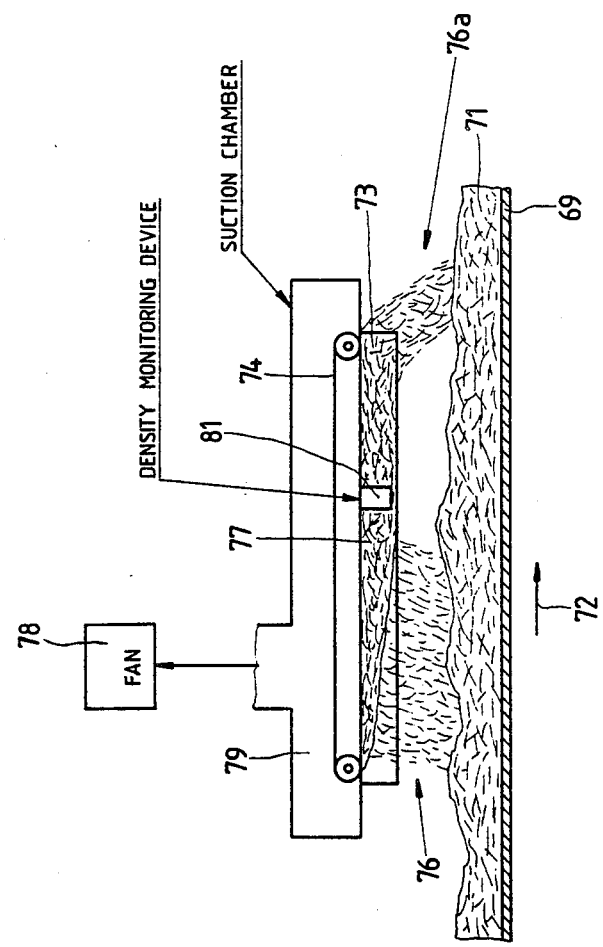
FIG. 4 is a fragmentary partly elevational and partly longitudinal vertical sectional view of a modified apparatus which monitors the density of stream of tobacco particles temporarily lifted off a continuous flow of fibrous material.

The method and apparatus of the present invention render it possible to determine the filling power of tobacco or other fibrous material which is transported by a vibratory conveyor or by analogous transporting means (such as the so-called fluidized bed conveyors). As shown in FIG. 4, the upper reach of an endless belt conveyor 69 or a vibrating or oscillating plate transports a stream or flow 71 of fibrous material in the direction of arrow 72. The upper surface of the flow 71 is disposed immediately or closely below the open lower end of a suction duct or channel 73 extending below the lower reach of an endless belt conveyor 74 corresponding to the conveyor 1. The upper end of the channel 73 is adjacent the air-permeable bottom wall of a suction chamber 79 which is connected with the intake of a fan 78 or another suitable suction generating device. The channel 73 is at least substantially parallel to the conveyor 69, and suction in the chamber 79 entails a lifting of particles 76 of tobacco from the flow 71 to form a stream 77 which is advanced with the lower reach of the conveyor 74. The pressure differential between the interior of the suction chamber 79 and the interior of the channel 73 below the conveyor 74 ensures that the stream 77 is densified on its way toward a position sensitive resolution density monitoring or measuring device 81 (which can be identical with the device 21) adjacent the path of movement of the stream 77. Signals which are transmitted by the transducer of the monitoring device 81 are or can be indicative of certain characteristics, especially the filling power, of tobacco particles 76. When the measurement is completed, the suction chamber 79 is disconnected from the suction generating device 78 and the particles 76 of the stream 77 leave the channel 73 in the form of a shower 76a which descends onto the stream 71 advancing with the conveyor 69.

The structure which is shown in FIG. 4 can be installed at any desired location adjacent the flow 71 which is used to form the stream 77, e.g., very close to the stream building zone so as to ensure that corrective measures can be undertaken (when necessary) before the flow 71 reaches the first processing station (such as the trimming station of FIG. 1).

The apparatus of FIG. 4 renders it possible to ascertain the density and/or filling power of tobacco even prior to completed making of the stream which is then converted into a cigarette rod or the like, i.e., at a very early stage of making of the stream. In other words, the density and filling power can be ascertained during treatment of tobacco ahead of the distributor of a cigarette rod making machine or the like i.e., during the so-called preparation stage of tobacco treatment.

The control circuit 22 can constitute a microprocessor or another computer with integrated totalizers, counters, comparators and other modules. The block diagram of FIG. 2 has been chosen in order to facilitate the understanding of the mode of operation of the control means.

In accordance with a presently preferred embodiment of the invention, the filling power calculator 51, the function generator 52 and the threshold circuit 53 of the branch 48 together constitute a microprocessor. The microprocessor processes signals from detectors 34 (i.e., signals denoting the densities of the corresponding layers A) on the basis of predetermined stored mathematical relationships with the volume of the stream, with the moisture contents of the fibers and (if necessary) the temperature of the fibers to generate signals which are indicative of the filling power, and such signals are processed in the same microprocessor. To this end, the microprocessor uses the aforediscussed hardness-density-filling power matrix containing information pertaining to different filling power values and corresponding hardness and density values. The processor withdraws from the matrix a density value (which corresponds to a given hardness) for each filling power signal, and such density value is then used in a manner as described above in connection with the operation of the branch 48. A processor of the type 8051 made by INTEL has been found to be useful as a means for performing the combined functions of the parts 51, 52 and 53 in the branch 48.

The circuit 32 may be of the type known as RC 1024 SA which is manufactured by RETICON-EG & G Instruments, München, German Federal Republic. The same firm manufactures a module known as 1024 SFX which can be used as the diode array of the density monitoring device 21. The diode array can be replaced with a CCD-array known as Line Scan Image Sensor Type CCD 143 DC which is manufactured by Fairchild.

The X-ray tube 26 constitutes but one of the radiation sources which can be used in the density monitoring device 21. It can be replaced with a source of ultrasonic, electronic or infrared radiation in conjunction with appropriate detectors without departing from the spirit of the invention. All that counts is to ensure that the selected device 21 can properly monitor the density of successive layers A of the stream 11 in a manner as described above in connection with the radiation source 26 and detectors 34 or in an analogous manner.

The preceding description of the measurement of filling power of tobacco is based on the premise that the suction at one side of the lower reach of the conveyor 1 or 74 is constant. This holds true in a great majority of oases. However, if the suction in the chamber 3 or 79 is altered to a considerable extent the change must be taken into consideration in the filling power calculator 51 because the intensity of suction acting upon the tobacco stream 11 or 77 is a factor which influences the density of the stream i.e., a parameter which is the basis of the calculation of filling power. In order to monitor the pressure in the suction chamber 3, the apparatus of FIGS. 1 to 3 further comprises a pressure monitoring device 3a which is installed in or adjacent the chamber 3 and transmits signals denoting the pressure in the chamber 3 to the filling power calculator 51.

It is further assumed that the temperature of tobacco, whose filling power is measured and calculated, is at least substantially constant. Since the temperature of the tobacco stream 11 or 77 also influences the Filling power, it is desirable and advantageous to monitor such temperature, at least when the temperature fluctuates within a reasonably wide range. Signals which denote the temperature of the tobacco stream are taken into consideration in calculating the filling power. To this end, the apparatus of FIGS. 1 to 3 comprises a thermometer 23a which is or can be adjacent the moisture detector 23 and whose signals are transmitted to the filling power calculator 51.

Without further analysis, the foregoing will so fully reveal the gist of the present invention that others can, by applying current knowledge, readily adapt it for various applications without omitting Features that, From the standpoint of prior art, fairly constitute essential characteristics of the generic and specific aspects of our contribution to the art and, therefore, such adaptation should and are intended to be comprehended within the meaning and range of equivalence of the appended claims.

We claim:

1. A method of making and processing a stream of fibrous material, such as particles of tobacco having a predetermined filling power, comprising the steps of advancing the stream longitudinally in a predetermined direction along a predetermined path; monitoring the densities of different layers in successive increments of the advancing stream in a succession of planes disposed at progressively increasing distances from a reference plane which bears a predetermined relationship to the path and generating first signals denoting the densities of the respective layers in successive increments of the stream; generating a second signal constituting the sum of those first signals which denote the densities of successive layers of said succession, starting with the layer nearest to said reference plane and terminating with a layer disposed at a predetermined distance from said reference plane; and converting the second signal into a third signal denoting the filling power of the fibrous material.

2. The method of claim 1, wherein said monitoring step includes measuring the densities of the layers at a plurality of locations forming a row extending substantially transversely of said direction.

3. The method of claim 1 of making and processing a stream which contains a surplus of fibrous material, further comprising the steps of converting the third signal into a reference signal denoting a predetermined density of the stream, monitoring the density of the stream and generating an additional signal denoting the actual density of the stream, removing the surplus from the stream to convert the latter into an equalized stream, converting the equalized stream into a filler having a hardness which is a function of the quantity of fibrous material in the equalized stream, comparing the reference signal with the additional signal and generating a further signal denoting the difference between the reference signal and the additional signal, and utilizing the further signal to change the quantity of removed surplus so as to maintain the hardness of the filler within a preselected range.

4. The method of claim 3, further comprising the step of maintaining the intensity of the reference signal within a predetermined range including reducing the intensity of the reference signal prior to said comparing step when such intensity exceeds the upper limit of said predetermined range and increasing the intensity of the reference signal prior to said comparing step when the intensity is below the lower limit of said predetermined range.

5. The method of claim 1, wherein said advancing step includes moving the stream by a conveyor having a stream contacting surface in said reference plane.

6. The method of claim 1 of making and processing a stream which contains a surplus of fibrous material, further comprising the steps of removing the surplus from the stream in a second plane spaced apart from said reference plane to form an equalized stream, monitoring the density of the stream portion which is located outside of the area between said planes and constitutes the surplus, and generating a signal denoting the quantity of such surplus.

7. The method of claim 6, further comprising the steps of directing fibrous material into said path at a variable rate to form the stream, and varying the rate of delivery of fibrous material as a function of changes in the characteristics of the signal denoting the quantity of the surplus so as to maintain the quantity of surplus in the stream within a given range.

8. The method of claim 7 further comprising the steps of converting the equalized stream into a filler, monitoring at least one quality of the filler which is dependent upon the quantity of the surplus, and selecting said given range so that its lower limit is sufficient to maintain said quality above a preselected minimum standard of acceptability.

9. The method of claim 8, wherein said quality monitoring step comprises generating signals denoting the monitored quality and further comprising the steps of establishing a reference signal denoting the minimum standard of acceptability, comparing the quality denoting signals with the reference signal denoting the minimum standard of acceptability, generating control signals denoting the difference between the compared signals, and using the control signals to regulate said selecting step.

10. The method of claim 9, further comprising the step of converting the filler into a succession of rod-shaped articles, said quality monitoring step including monitoring the articles.

11. The method of claim 10, wherein said article monitoring step includes ascertaining the densities of selected portions of the articles.

12. The method of claim 1, further comprising the steps of transporting a flow of fibrous material along a second path and transferring a portion of the flow from said second path into said predetermined path to form said stream.

13. The method of claim 12, wherein transferring step includes lifting said portion of the flow by a suction conveyor, advancing the lifted portion of the flow in suspended condition along said predetermined path, and pneumatically condensing the lifted portion at least in the course of said density monitoring step.

14. The method of claim 12, further comprising step of returning the stream into said second path upon completion of said density monitoring step.

15. A method of making and processing a stream of fibrous material, such as particles of tobacco, which contains a surplus of fibrous material, comprising the steps of advancing the stream longitudinally by the stream-contacting surface of a conveyor in a predetermined direction along a predetermined path; monitoring the densities of different layers of the advancing stream in a succession of planes disposed at progressively increasing distances from a reference plane which bears a predetermined relationship to the contacting surface and generating first signals denoting the densities of the respective layers; removing the surplus from the stream in a plane of removal which is spaced apart from the reference plane to form an equalized stream; establishing a reference signal denoting a predetermined density; generating a series of third signals constituting the sums of those first signals which denote the densities of successive layers of said succession, starting with the layer nearest to said reference plane; comparing successive third signals with the reference signal; and utilizing that one third signal which at least matches the reference signal to shift the plane of removal to a plane correlated to the plane of that layer whose monitoring has produced the first signal the addition of which to preceding first signals has resulted in the generation of said one third signal.

16. The method of claim 16 of making and processing a stream of fibrous material having a predetermined filling power, wherein said step of establishing said reference signal includes converting a third signal which is the sum of a preselected number of first signals into a fourth signal denoting the filling power of the fibrous material and converting said fourth signal into said reference signal.

17. The method of claim 15, wherein said reference surface is the stream-contacting surface of the conveyor.

18. The method of claim 15, further comprising the step of generating a fourth signal denoting the quantity of the surplus and the sum of those first signals which represent the densities of layers outside of the area between said reference plane and said plane of removal.

19. The method of claim 18, further comprising the steps of directing fibrous material into said path at a variable rate to form the stream, and varying the rate of delivery of fibrous material as a function of changes of the characteristics of said fourth signal so as to maintain the quantity of the surplus within a given range.

20. The method of claim 19, further comprising the steps of converting the equalized stream into a filler, monitoring at least one quality of the filler which is dependent upon the quantity of the surplus, and selecting said given range so that its lower limit is sufficient to maintain said quality above a predetermined minimum standard of acceptability.

21. The method of claim 20, wherein said quality monitoring step comprises generating signals denoting the monitored quality and further comprising the steps of establishing a reference signal denoting the minimum standard of acceptability, comparing the quality denoting signals with the reference signal denoting the minimum standard of acceptability, generating control signals denoting the difference between the compared signals, and using the control signals to regulate said selecting step.

22. The method of claim 21, further comprising the step of converting the filler into a succession of rod-shaped articles, said quality monitoring step including monitoring the articles.

23. The method of claim 22, wherein said article monitoring step includes ascertaining the densities of selected portions of the articles.

24. The method of claim 15, further comprising the steps of transporting a flow of fibrous material along a second path and transferring a portion of the flow from said second path into said predetermined path to form said stream.

25. The method of claim 24, wherein said transferring step includes lifting said portion of the flow by the conveyor, advancing the lifted portion of the flow in suspended condition along said predetermined path, and pneumatically condensing the lifted portion at least in the course of said density monitoring step.

26. The method of claim 24, further comprising the step of returning the stream into said second path upon completion of said density monitoring step.

27. Apparatus for making and processing a stream of fibrous material, such as particles of tobacco, having a predetermined filling power, comprising a conveyor defining a predetermined path; means for delivering fibrous material into a first portion of said path so that the particles accumulate and form the stream which advances along said path; means for monitoring the densities of different layers of the stream downstream of said first portion in a succession of planes disposed at progressively increasing distances from said conveyor, including at least one row of detectors extending transversely of said path and each arranged to generate a first signal denoting the density of the adjacent layer of the stream; and control means for evaluating said first signals including totalizing means for forming a second signal denoting the sum of a predetermined number of first signals generated by said detectors starting with the detector nearest to said conveyor, and calculator means for converting said second signal into a third signal denoting the filling power of fibrous material.

28. The apparatus of claim 27, wherein each of said detectors includes a position sensitive transducer and said monitoring means further comprises a source of radiation which penetrates through the stream to an extent which is a function of the density of the layers and is directed upon said detectors.

29. The apparatus of claim 27 for making and processing a stream which contains a surplus of fibrous material, further comprising adjustable means for removing the surplus from the stream in a second portion of said path downstream of said first portion so that the stream is converted into an equalized stream, means for converting the equalized stream into a filler including means for densifying the stream, said control means further comprising function generator means for converting the third signal into a fourth signal denoting a predetermined density of the filler, and means for adjusting said removing means as a function of said fourth signal when the hardness of the filler deviates from a predetermined hardness.

30. The apparatus of claim 29, further comprising a threshold circuit connected with said function generator means and having means for maintaining the intensity of said fourth signal within a predetermined range.

31. The apparatus of claim 29, further comprising a source of reference signals denoting a predetermined hardness of the filler and arranged to transmit such signals to said function generator means.

32. The apparatus of claim 29, further comprising means for generating additional signals denoting the moisture content of fibrous material in the stream and for transmitting such additional signals to said function generator means to influence said fourth signal.

33. The apparatus of claim 32, wherein said function generator means comprises an empirically ascertained moisture-density matrix which influences said fourth signal as a function of said additional signals.

34. The apparatus of claim 27, wherein said monitoring means further comprises a source of X-rays arranged to direct X-rays against the stream so that the rays penetrate through and impinge upon said detectors with an intensity which is a function of the density of the respective layers.

35. The apparatus of claim 27, wherein said detectors include a unidimensional array of diodes.

36. The apparatus of claim 27, wherein said detectors constitute a CCD-array.

37. The apparatus of claim 27, wherein said delivering means includes means for transporting a flow of fibrous material along a second path at a level below said predetermined path, said conveyor including means for transferring a portion of said flow from said second path into said predetermined path so that the transferred portion of the flow constitutes the stream.

38. The apparatus of claim 37, wherein said conveyor includes an endless foraminous belt having a lower reach adjacent said predetermined path and a suction chamber disposed above said reach and arranged to attract said portion of the flow against said lower reach and to attract the stream to said lower reach during advancement past said monitoring means.

39. The apparatus of claim 27 for making and processing a stream which contains a surplus of fibrous material, further comprising adjustable means for removing the surplus from the stream in a second portion of said path downstream of said first portion so as to convert the stream into an equalized stream, means for converting the equalized stream into a filler including means for densifying the equalized stream, said control means comprising second totalizing means for generating a series of fourth signals constituting the sums of those first signals which denote the densities of successive layers of said succession, starting with the layer nearest to said conveyor, function generator means for converting the third signal into a fifth signal denoting a predetermined density of the stream, means for comparing successive fourth signals with said fifth signal and for generating sixth signals denoting the difference between said fourth signals and said fifth signal, and means for adjusting said removing means as a function of that sixth signal which at least matches said fifth signal.

40. The apparatus of claim 39, wherein said control means further comprises third totalizing means for generating a seventh signal denoting the sum of all first signals indicating the density of the surplus, means for establishing a reference signal denoting the desired quantity of the surplus, means for comparing said seventh signal with said reference signal and for generating a further signal, and means for adjusting the delivering means as a function of said further signal so as to maintain the quantity of the surplus within a predetermined range.

41. The apparatus of claim 40, further comprising means for monitoring a quality of the filler which is dependent upon the quantity of the surplus and for influencing said further signal.

42. The apparatus of claim 41, further comprising means for converting the filler into a series of rod-shaped articles, said quality monitoring means including means for monitoring a quality of the articles and said influencing means including means for maintaining the surplus at a value such that the quality of the articles remains above a minimum standard of acceptability.

43. Apparatus for making and processing a stream of fibrous material, such as particles of tobacco, comprising a conveyor defining a predetermined path; means for delivering fibrous material into a first portion of said path so that the particles accumulate and form a stream which contains a surplus of fibrous material and advances along said path; adjustable means for removing the surplus in a first plane spaced apart from said conveyor in a second portion of said path downstream of said first portion so that the stream is converted into an equalized stream; means for monitoring the densities of different layers of the stream between said first and second portions in a succession of planes disposed at progressively increasing distances from said conveyor, including detectors forming at least one row extending transversely of said path, each of said detectors being arranged to generate a first signal denoting the density of the adjacent layer; and control means for evaluating said first signals including totalizing means for generating a series of second signals constituting the sums of those first signals which denote the densities of successive layers of said succession starting with the layer nearest said conveyor, a source of reference signals denoting a predetermined density of the stream, means for comparing successive second signals with said reference signals, and means for adjusting said removing means in response to generation of that second signal which at least matches said reference signals.

44. The apparatus of claim 43, wherein each of said layers is disposed in a different plane and said adjusting means includes means for moving said removing means to that one of said different planes which contains the layer whose monitoring and totalizing has resulted in the generation of the second signal at least matching said reference signals.

45. The apparatus of claim 43, wherein said control means further comprises second totalizing means for generating a fifth signal denoting the sum of all first signals indicating the density of the surplus of fibrous material, means for establishing a second reference signal denoting the desired quantity of the surplus, means for comparing said second reference signal with said fifth signal and for generating a seventh signal, and means for adjusting said delivering means as a function of said seventh signal so as to maintain the quantity of the surplus within a predetermined range.

46. The apparatus of claim 45, further comprising means for converting the equalized stream into a filler, means for monitoring a quality of the filler which is dependent upon the quantity of the surplus and for influencing said seventh signal.

47. The apparatus of claim 46, further comprising means for converting the filler into a series of rod-shaped articles, said quality monitoring means including means for monitoring a quality of the articles and said influencing means including means for maintaining the surplus at a value such that the quality of the articles remains above a minimum standard of acceptability.

48. The apparatus of claim 43, wherein said monitoring means further comprises a source of X-rays arranged to direct radiation against the stream so that the radiation penetrates through the stream and impinges upon said detectors with an intensity which is a function of the density of the respective layers.

49. The apparatus of claim 43, wherein said detectors include a unidimensional array of diodes.

50. The apparatus of claim 43, wherein said detectors constitute a CCD-array.

51. The apparatus of claim 43, wherein said delivering means includes means for transporting a flow of fibrous material along a second path at a level below said predetermined path, said conveyor including means for transferring a portion of said flow from said second path into said predetermined path so that the transferred portion of the flow constitutes the stream.

52. The apparatus of claim 51, wherein said conveyor includes an endless foraminous belt having a lower reach adjacent said predetermined path and a suction chamber disposed above said reach and arranged to attract said portion of the flow against said reach and to attract the stream to said reach during advancement past said monitoring means.

* * * * *